United States Patent [19]

Rosenbaum et al.

[11] Patent Number: 5,034,213

[45] Date of Patent: Jul. 23, 1991

[54] PHOTOSTABLE COSMETIC COMPOSITION CONTAINING AN ETHYLRUTIN DERIVATIVE AS PROTECTIVE AGENT AGAINST SUNLIGHT AND ITS USE IN THE PROTECTION OF THE SKIN AND THE HAIR

[75] Inventors: Georges Rosenbaum, Asnieres; Jean F. Grollier, Paris, both of France

[73] Assignee: L'Oreal, Paris, France

[21] Appl. No.: 357,728

[22] Filed: May 26, 1989

Related U.S. Application Data

[63] Continuation of Ser. No. 100,082, Sep. 22, 1987, abandoned.

[30] Foreign Application Priority Data

Sep. 22, 1986 [LU] Luxembourg ............................ 86601

[51] Int. Cl.$^5$ .......................... A61K 7/40; A61K 7/42; A61K 7/44; A61K 9/12
[52] U.S. Cl. ............................................ 424/47; 8/405; 8/406; 424/DIG. 1; 424/DIG. 2; 424/DIG. 5; 424/59; 424/60; 424/61; 424/62; 424/63; 424/64; 424/70; 424/71; 424/72; 514/844; 514/847; 514/938; 514/944; 514/945; 514/969
[58] Field of Search .................. 424/59, 70, 47, 60, 424/63; 536/8; 8/405, 406

[56] References Cited

U.S. PATENT DOCUMENTS

| | | | |
|---|---|---|---|
| 2,646,428 | 7/1953 | Chabrier et al. | 536/8 |
| 2,890,225 | 6/1959 | Gregory | 424/59 |
| 3,311,636 | 3/1967 | Moffett | 424/59 |
| 3,516,884 | 6/1970 | Courbat | 536/8 |
| 3,625,976 | 12/1971 | Theimer | 424/59 |
| 4,603,046 | 7/1986 | Georgalas et al. | 536/8 |

FOREIGN PATENT DOCUMENTS

| | | | |
|---|---|---|---|
| 1434376 | 2/1966 | France | 536/8 |
| 423808 | 11/1966 | Switzerland | 536/8 |

OTHER PUBLICATIONS

Frantisek, Chem. Abs. 1985, vol. 102, p. 185433j.
Lecomte, Chem. Abs., 1972, vol. 75, p. 108217j.
Merck Index, 1952, 6th Edition, pp. 840 and 841.
Sagarin, Cosmetics Science and Technology, 1957, pp. 199–203.

*Primary Examiner*—Dale R. Ore
*Attorney, Agent, or Firm*—Cushman, Darby & Cushman

[57] ABSTRACT

Photostable cosmetic composition containing an ethylrutin derivative as protective agent against sunlight and its use in the protection of the skin and the hair.

The invention relates to a photostable cosmetic composition for the protection against UV rays with wavelengths between 280 and 400 nm, which contains an effective quantity of an ethylrutin derivative chosen from amongst tetrahydroxyethylurtin and morpholinoethylrutin, in a cosmetically acceptable aqueous or aqueous/alcoholic medium.

The ethylrutin derivative is advantageously combined with a know UV-B or UV-A filter.

Application as a sunscreen composition for skin, a protective composition for hair as a light-stabilized cosmetic composition.

13 Claims, No Drawings

PHOTOSTABLE COSMETIC COMPOSITION CONTAINING AN ETHYLRUTIN DERIVATIVE AS PROTECTIVE AGENT AGAINST SUNLIGHT AND ITS USE IN THE PROTECTION OF THE SKIN AND THE HAIR

This is a continuation of application Ser. No. 07/100,082, filed Sept. 22, 1987, now abandoned.

Photostable cosmetic composition containing an ethyl-rutin derivative as protective agent against sunlight and its use in the protection of the skin and the hair.

The present invention relates to a photostable cosmetic composition for protection against ultraviolet rays containing an ethylrutin derivative and to its use in the protection of the skin and the hair.

It is well known that the skin is sensitive to solar radiations which can cause a simple sunburn or erythema, but which may also cause burns of varying degrees of intensity.

However, solar radiations also have other harmful effects such as a loss of skin elasticity and the appearance of wrinkles leading to a premature ageing. Even dermatoses may sometimes be observed. The extreme case is the occurrence of skin cancers in some subjects.

It is also desirable to ensure the provision to hair of a good protection against photochemical degradation in order to prevent a change in shade, a discoloration or a degradation of mechanical properties.

Moreover, it is known that the constituents which form part of cosmetic preparations, and in particular some dyestuffs in dyeing compositions, colored hair lacquers, shampoos, hair setting lotions and make-up products such as tinted creams, nail varnishes and lipsticks, do not always have a sufficient light-stability, and that they become degraded under the influence of light radiations.

It is well known that the most dangerous part of solar radiation consists of ultraviolet radiations with wavelengths less than 400 nm. It is also known that because of the presence of the ozone layer in the terrestrial atmosphere which absorbs a part of the solar radiation, the lower limits for the ultraviolet radiation reaching the earth's surface is in the region of 280 nm.

Consequently, it seems desirable to have available compounds capable of absorbing ultraviolet radiations within the wavelength range from 280 to 400 nm, i.e. UV-B rays with wavelengths between 280 and 320 nm which play a preponderant role in causing solar erythema, as well as UV-A rays with wavelengths between 320 and 400 nm which cause a browning of the skin and also the ageing thereof, and which promote the onset of erythematous reaction or enhance this reaction in some subjects or which may even be at the origin of photo-toxic or photo-allergic reactions.

The use of substances which filter these ultraviolet radiations, in particular for protecting the skin against the harmful effects of sunlight, has already been recommended. Among these substances, some flavanoids and especially quercetin and rutin, are known.

Flavanoids cover a wide range of structures which are classified into:
flavones and flavonols;
isoflavones, flavanones and dihydroflavonols;
chalcones and aurones; and
anthocyanidins and anthocyanins.

However, the production of compositions which are effective in offering protection against UV rays requires substances which filter within the wavelength range between 280 and 400 nm, which ensure a high degree of protection and which are at the same time sufficiently soluble in commonly used cosmetic media and stable against oxidation and against degradation due to atmospheric agents.

However, none of the compounds which belong to the classes mentioned above has the properties of ultraviolet radiation absorption within the range mentioned, sufficient solubility and photostability, which are required for them to be able to contribute to the preparation of compositions which give a sufficiently effective protection against ultraviolet radiations.

Water-soluble anthocyanidins and anthocyanins absorb outside the range of UV radiations reaching the earth's surface, viz. between 270 and 280 nm and in the visible range, viz. between 465 and 550 nm.

The remaining compounds mentioned above, for their part, indeed absorb within the range of UV radiations in question; however, they have the disadvantage of being practically insoluble in water, especially when these are polyhydroxylated compounds. These compounds are slightly more soluble in water when they are in the glucoside, diglucoside, rhamnoside, rhamnoglucoside or galactoside form and in a general way, in the 0-glucoside form. However, this increase in solubility still proves to be insufficient for these compounds to be able to contribute to the preparation of compositions which protect effectively against UV radiations within the range under consideration.

Now, the applicants have discovered, in a surprising way, that contrary to all expectations, some ethylrutin derivatives had a wide filtering power in the ultraviolet range within the wavelength range between 280 and 400 nm, a good solubility in water and a good stability against UV rays at the same time and they thus ensured a good protection against UV rays.

Therefore, the subject of the present invention is a photostable cosmetic composition which protects against ultraviolet rays with wavelengths between 280 and 400 nm, which contains an effective quantity of at least one ethylrutin derivative chosen from amongst tetrahydroxyethylrutin and morpholinoethylrutin, in a cosmetically acceptable aqueous or aqueous/alcoholic vehicle.

In the description which follows, the term "ethylrutin derivative" will be used to denote tetrahydroxyethylrutin and morpholinoethylrutin.

These sunscreens according to the invention have the important additional advantage of being well tolerated by the skin and of offering useful cosmetic properties.

Another subject of the invention consists of a method for protecting the skin and the hair, which may be natural or sensitized, against solar radiation, which consists in applying to the skin or the hair an effective quantity of at least one ethylrutin derivative.

"Sensitized hair" means hair which has undergone a permanent-waving, dyeing or bleaching treatment.

The invention also relates to a method for protecting a colored or uncolored cosmetic composition against solar radiation, which consists in incorporating into such a composition an effective quantity of at least one ethylrutin derivative.

The ethylrutin derivative is present in the cosmetic composition according to the invention in proportions of between 0.1 and 20% relative to the total weight of the composition and preferably between 0.5 and 10%.

The ethylrutin derivative may be combined with other known sunscreens which are specific to UV-B radiation and/or UV-A radiation, especially when the cosmetic composition constitutes a sunscreen composition. A reinforced formulation which filters the whole of the UV-B and the UV-A radiations may therefore be obtained in this way. In this case, the ethylrutin derivative and the other known sunscreens are contained in the sunscreen composition in total proportions of between 0.1 and 20% relative to the total weight of the composition.

The ethylrutin derivative employed according to the invention may be combined with UV-B filters which consist of lipid-soluble compounds or of oils with filtering properties, such as, in particular, coffee-bean oil. As lipophilic UV-B sunscreens, there may be mentioned salicylic acid esters such as 2-ethylhexyl salicylate, homomenthyl salicylate, cinnamic acid esters such as 2-ethylhexyl p-methoxycinnamate, 2-ethoxyethyl p-methoxycinnamate and p-aminobenzoic acid esters such as amyl p-aminobenzoate and 2-ethylhexyl p-dimethylaminobenzoate, benzophenone derivatives such as 2-hydroxy-4-methoxybenzophenone or 2,2'-dihydroxy-4-methoxybenzophenone, and 3-benzylidenecamphor and 3-(4'-methylbenzylidene)camphor.

As water-soluble sunscreens which filter UV-B rays, which may also be combined with the ethylrutin derivative according to the invention, there may be mentioned the benzylidenecamphor derivatives described in French Patent Nos. 2,199,971, 2,236,515, 2,282,426 and 2,383,904 of the Applicants and more particularly 4-(2-oxo-3-bornylidenemethyl)phenyltrimethylammonium methylsulphate as well as 4-(2-oxo-3-bornylidenemethyl)benzenesulphonic acid, 2-methyl-5-(2-oxo-3-bornylidenemethyl)benzenesulphonic acid, 3-benzylidene-2-oxo-10-bornanesulphonic acid and 2-phenylbenzimidazole-5-sulphonic acid and the metal or ammonium salts thereof.

The compounds according to the invention may also be combined with UV-A filters among which there may be mentioned, in particular, dibenzoylmethane derivatives and benzene-1,4-[di(3-methylidenecamphor)] derivatives sulphonated on the methyl radical in position 10 of the camphor as described in French Patent No. 2,528,420.

It is understood that the list of sunscreens employed in combination with the sunscreen according to the invention, which is mentioned above, is not limiting.

The ethylrutin derivative is solubilized in water or in an aqueous/alcoholic solution. The more particularly preferred monohydric or polyhydric alcohols contain 1 to 6 carbon atoms and are chosen from amongst ethanol, isopropanol, propylene glycol, glycerol and sorbitol and the aqueous/alcoholic solutions are preferably mixtures of water and ethanol.

The composition according to the invention may be in the various forms commonly employed in this type of composition. It may especially be present dissolved in the form of a lotion thickened to a variable extent, as an emulsion in the form of a cream or a milk, in the form of a pomade or in the form of a gel, or may be packaged as an aerosol.

When the cosmetic composition according to the invention is in the form of an emulsion which forms a sunscreen composition, it is advantageous to dissolve a liposoluble sunscreen in the fatty phase, the ethylrutin derivative, for its part, being dissolved in the aqueous phase.

According to a first embodiment, the cosmetic composition according to the invention is intended to be applied onto the skin and contains cosmetic adjuvants commonly employed in this type of composition. As examples of this, there may be mentioned, fats such as mineral, animal, vegetable or synthetic oils or waxes, fatty acids, fatty acid esters such as triglycerides or fatty acids containing from 8 to 18 carbon atoms, and fatty alcohols; emulsifiers and thickeners.

Among mineral oils, there may be mentioned liquid petrolatum; among animal oils, there may be mentioned whale, seal, menhaden, halibut liver, cod liver, tuna, turtle, suet, neat's-foot, horse's-foot, sheep's-foot, mink, otter and marmot oils; among vegetable oils, there may be mentioned almond, peanut, wheatgerm, olive, corn, jojoba, sesame, sunflower, palm and walnut oils.

Among fatty acid esters, there may be mentioned isopropyl esters of myristic, palmitic and stearic acids and fatty esters which are solid at 25° C.

Fats such as vaseline, paraffin, lanolin, hydrogenated lanolin, acetylated lanolin and silicone fluids may also be employed.

Among waxes, there may be mentioned Sipol wax, lanolin wax, beeswax, candelilla wax, microcrystalline wax, carnauba wax, spermaceti, cocoa butter, karite nut butter, silicone waxes, hydrogenated oils which are solid at 25° C., sugar glycerides, and oleates, myristates, linoliates and stearates of Ca, Mg, Zn and Al.

Among fatty alcohols, there may be mentioned lauryl, cetyl, myristyl, stearyl, palmityl and oleyl alcohols.

Among emulsifiers, which may be nonionic, anionic, cationic or amphoteric, there may be mentioned, polyoxyethylenated or polyglycerolated fatty alcohols such as, for example, lauryl, cetyl, stearyl and oleyl alcohols containing from 2 to 30 moles of ethyleneoxide.

Among thickeners, there may be mentioned cellulose derivatives, polyacrylic acid derivatives, and guar, carob and xanthan gums.

The cosmetic composition according to the invention may also contain other adjuvants commonly employed in cosmetics and especially moisturizers, softeners, coloring agents, opaquing agents, preservatives and perfumes.

It may optionally contain a pH regulating agent. The pH is between 4 and 9 and preferably between 5.5 and 8.

In the case of a composition which is packaged as an aerosol, conventional propellants such as alkanes, fluoroalkanes and chlorofluoroalkanes are employed.

According to another embodiment, the cosmetic composition according to the invention is intended for protecting natural or sensitized hair against UV rays. This composition may be in the form of a shampoo, a lotion, a gel or an emulsion to be rinsed, to be applied before or after shampooing, before or after dyeing or bleaching, before or after permanent-waving, a hair-styling or treatment lotion or gel, a blow-drying or setting lotion or gel, a hair lacquer or a composition for permanent-waving, dyeing or bleaching the hair. In addition to the compound of the invention, this composition may contain various adjuvants commonly employed in this type of composition, such as surface-active agents, thickeners, polymers, softeners, preservatives, foam stabilizers, electrolytes, organic solvents, silicone derivatives, oils, waxes, antigrease agents or dyestuffs and/or pigments which have the role of coloring the composition itself, or the hair, or any other ingredient which is commonly employed in the field of hair.

When the composition consists of a shampoo, the latter is essentially characterized in that it contains at least one anionic, nonionic or amphotoric surface-active agent or mixture thereof and a compound according to the invention, in an aqueous medium.

When the composition consists of an unrinsed lotion—blow-drying lotion, hair setting lotion or hair-styling or treatment lotion—in addition to the compound according to the invention, it generally contains in an aqueous or aqueous/alcoholic solution at least one cationic, anionic, nonionic or amphoteric polymer or mixture thereof, in quantities between 0.1 and 10%, and preferably between 0.1 and 3% by weight, and optionally antifoaming agents.

When the composition constitutes a rinsed lotion, also called a rinse, it is applied before or after dyeing or bleaching, before or after permanent-waving, before or after shampooing or between two stages of shampooing, and then rinsed after an exposure time.

This composition may be an aqueous or aqueous/alcoholic solution optionally containing surfactants, an emulsion or a gel. This composition may also be pressurized as an aerosol.

The invention also relates to a cosmetic composition, the UV-ray sensitive constituents of which are protected against light radiations by the presence of at least one ethylrutin derivative, in an effective quantity which is generally between 0.1 and 10% by weight.

This composition containing one or more compounds which are particularly sensitive to ultraviolet rays, may be a capillary composition such as a hair lacquer, a colored or uncolored hair setting lotion, a shampoo, a coloring shampoo, a hair dyeing composition, or alternatively a make-up product such as a nail varnish, a make-up foundation, a lipstick or a skin treatment cream and in a general way, any cosmetic composition which may present light-stability problems during storage because of its constituents.

The following examples illustrate the invention without, however, limiting it.

EXAMPLE 1

A sunscreen gel with the following composition is prepared:

| | |
|---|---|
| Morpholinoethylrutin | 4.00 g |
| Crosslinked polyacrylic acid, MW = 3 million, Sold under the name CARBOPOL 934 by GOODRICH | 0.80 g |
| Glycerin | 12.00 g |
| Ethyl alcohol | 15.00 g |
| Triethanolamine | 5.00 g |
| Water | qs 100.00 g |

EXAMPLE 2

A sunscreen cream (W/O emulsion) with the following composition is prepared:

| | |
|---|---|
| Morpholinoethylrutin | 1.50 g |
| 3-Benzylidene-d,l-camphor | 2.00 g |
| Hydroxyoctacosanyle hydroxystearate | 10.00 g |
| Polyoxyethylenated hydrogenated castor oil, containing 7 moles of ethylene oxide | 9.00 g |
| Mixture of beeswax, ceresin wax and sorbitol sesquioleate | 2.25 g |
| Liquid petrolatum | 22.00 g |

-continued

| | |
|---|---|
| Glycerin | 5.00 g |
| Imidazolidinylurea derivative sold under the name GERMALL 115 by SUTTON LABS | 0.20 g |
| Perfume qs | |
| Water | qs 100.00 g |

EXAMPLE 3

A sunscreen cream (O/W emulsion) with the following composition is prepared:

| | |
|---|---|
| Morpholinoethylrutin | 2.00 g |
| 4-(2-Oxo-3-bornylidenemethyl)benzene-sulphonic acid | 3.50 g |
| Mixture containin 80% of cetylstearyl alcohol and 20% of oxyethylenated cetyl-stearyl alcohol containing 33 moles of ethyleneoxide | 6.50 g |
| Non-self-emulsifiable glycerol mono- and distearate mixture | 2.00 g |
| Cetyl alcohol | 1.70 g |
| Liquid petrolatum | 12.00 g |
| Propylene glycol | 2.50 g |
| Triethanolamine qs pH = 7 | |
| Preservative, perfume qs | |
| Water | qs 100.00 g |

EXAMPLE 4

A sunscreen milk (O/W emulsion) with the following composition is prepared:

| | |
|---|---|
| Morpholinoethylrutin | 2.50 g |
| 2-ethylhexyl p-methoxycinnamate (PARSOL MCX) | 2.50 g |
| Cetyl alcohol | 1.00 g |
| Oxyethylenated oleocetyl alcohol containing 30 moles of ethylene oxide | 5.00 g |
| Stearyl alcohol | 4.00 g |
| Palmitic ester of 2-ethylhexyl glyceryl ether | 2.00 g |
| Purcellin oil (stearyl octanoate) | 2.00 g |
| Liquid petrolatum | 8.00 g |
| Propylene glycol | 4.00 g |
| Preserative, perfume qs | |
| Water | qs 100.00 g |

EXAMPLE 5

A sunscreen milk (O/W emulsion) with the following composition is prepared:

| | |
|---|---|
| Tetrahydroxyethylrutin | 4.00 g |
| 4-(2-Oxo-3-bornylidenemethyl)benzenesulphonic acid | 2.00 g |
| Cetyl alcohol | 1.00 g |
| Oxyethylenated oleocetyl alcohol containing 30 moles of ethylene oxide | 5.00 g |
| Stearyl alcohol | 4.00 g |
| Palmitic ester of 2-ethylhexyl glyceryl ether | 2.00 g |
| Purcellin oil (stearyl octanoate) | 2.00 g |
| Liquid petrolatum | 8.00 g |
| Propylene glycol | 4.00 g |
| Triethanolamine qs pH = 6 | |
| Preservative, perfume qs | |
| Water | qs 100.00 g |

We claim:

1. In a photostable sunscreen cosmetic composition for application to the hair or skin to protect said hair or skin against UV-rays, said composition consisting essentially of, in a cosmetically acceptable aqueous or aqueous-alcoholic medium a protective agent against sunlight and at least one cosmetic adjuvant selected from the group consisting of a lower monohydric alcohol containing 1-6 carbon atoms, a lower polyhydric alcohol containing 1-6 carbon atoms, a mineral oil, a mineral wax, an animal oil, an animal wax, a vegetable oil, a vegetable wax, a synthetic oil, a synthetic wax, a fatty acid, a fatty acid ester, a fatty alcohol, an emulsifier, a thickener, a moisturizer, a softener, a coloring agent, an opaquing agent, a preservative, a perfume, a pH regulating agent and a propellant, wherein the improvement comprises as said protective agent against sunlight, a hair or skin protecting amount of an ethylrutin derivative selected from the group consisting of tetrahydroxyethylrutin and morpholinoethylrutin, said derivative having a wide filtering power between 280 and 400 nm.

2. The composition of claim 1 wherein said ethylrutin derivative is present in an amount ranging from 0.1 to 20 weight percent based on the total weight of said composition.

3. The composition of claim 1 which contains at least one said ethylrutin derivative and at least one other sunlight filtering agent, in a total amount ranging from 0.1 to 20 weight percent based on the total weight of said composition.

4. The composition of claim 3 wherein said other sunlight filtering agent is a UV-B filter selected from the group consisting of coffee bean oil, salicylic acid ester, cinnamic acid ester, p-aminobenzoic acid ester, a benzophenone, 3-benzylidenecamphor, 3-(4'-methylbenzylidene)camphor, 4-(2-oxo-3-bornylidenemethyl) phenyltrimethylammonium methylsulfate, 4-(2-oxo-3-bornylidenemethyl) benzenesulphonic acid, 2-methyl-5-(2-oxo-3-bornylidenemethyl) benzenesulphonic acid, 2-phenylbenzimidazole-5-sulphonic acid, 3-benzylidene-2-oxo-10-bornanesulphonic acid and a metal or ammonium salt thereof.

5. The composition of claim 3 wherein any remaining sunlight filtering agent is a UV-A filter selected from the group consisting of a dibenzoylmethane and a benzene-1,4-[di(3-methylidenecamphor)] sulphonated on the methyl radical in position 10 of the camphor.

6. The composition of claim 1 having a pH between 4 and 9.

7. The composition of claim 1 having a pH between 5.5 and 8.

8. The composition of claim 1 in the form of a lotion, an emulsion, a pomade, a gel or an aerosol.

9. The composition of claim 1 for application to the hair in the form of a shampoo, a lotion, a gel or an emulsion to be rinsed, a hairstyling lotion, a blow-drying or setting lotion or gel, or a hair lacquer.

10. The composition of claim 9 which also contains at least one cosmetic adjuvant selected form the group consisting of a surface-active agent, a thickener, a polymer, a softener, a preservative, a foam stabilizer, an electrolyte, an organic solvent, a silicone derivative, an oil, a wax, an anti-grease agent, a coloring agent and a pigment.

11. The composition of claim 1 in the form of a light-stabilized colored or colorless cosmetic composition comprising a hair lacquer, a colored or colorless hair setting lotion, a shampoo, a coloring shampoo, a hair dyeing composition or a make-up product, said composition containing from 0.1 to 10 percent by weight of at least one said ethylrutin derivative.

12. In a method for protecting the skin or hair against sunlight comprising applying to said skin or hair a sunlight protecting amount of a photostable sunscreen cosmetic composition, wherein the improvement comprises applying to said skin or hair the sunscreen cosmetic composition of claim 1.

13. In a process for protecting the skin or hair against UV rays comprising applying to said skin or hair a photostable sunscreen cosmetic composition, wherein the improvement comprises applying to said skin or hair, as said sunscreen cosmetic composition, a composition comprising in a cosmetically acceptable aqueous or aqueous/alcoholic medium a skin or hair protective amount of an ethylrutin derivative selected from the group consisting of tetrahydroxyethylrutin and morpholinoethylrutin, said composition providing protection against UV rays within a wide wavelength range between 280 and 400 nm.

* * * * *